Figure 1:
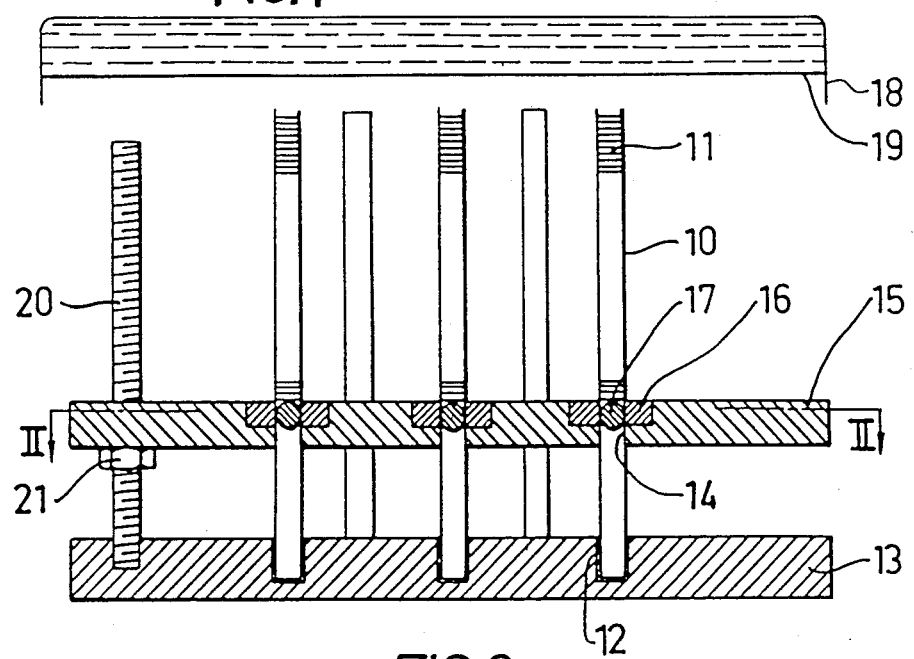

United States Patent [19]

Ericsson

[11] Patent Number: 4,643,795
[45] Date of Patent: Feb. 17, 1987

[54] METHOD AND DEVICE FOR APPLICATION OF OBJECTS ONTO A SURFACE

[75] Inventor: Magnus Ericsson, Stockholm, Sweden

[73] Assignee: AB Biodisk, Solna, Sweden

[21] Appl. No.: 734,164

[22] Filed: May 15, 1985

[30] Foreign Application Priority Data

May 16, 1984 [SE] Sweden .............................. 8402646

[51] Int. Cl.⁴ .............................................. B65C 9/10
[52] U.S. Cl. .................................. 156/562; 156/565; 156/573; 156/DIG. 29; 271/901
[58] Field of Search ....... 156/573, 564, 565, DIG. 29, 156/560, 562; 271/901

[56] References Cited

U.S. PATENT DOCUMENTS

| | | | |
|---|---|---|---|
| 3,565,722 | 2/1971 | Drake | 156/564 |
| 3,890,185 | 6/1975 | Umazume | 156/565 |
| 3,919,039 | 11/1975 | Rohner | 156/562 |
| 4,127,432 | 11/1978 | Kuwano et al. | 156/565 |
| 4,387,508 | 6/1983 | Wyatt | 271/901 |

FOREIGN PATENT DOCUMENTS 3116926  11/1982  Fed. Rep. of Germany .

*Primary Examiner*—Michael Wityshyn
*Attorney, Agent, or Firm*—Cushman, Darby & Cushman

[57] ABSTRACT

This invention relates to a method and device for applying an object (11), e.g. an antibiotic patch onto a receiving adhesive surface (19), e.g. an agar surface. The objects (11) are piled in a storage container (10), which is upwardly open, and the receiving surface (19) located above this is turned downwards. For application of the object (11) onto the surface (19) the whole pile is lifted towards the surface while the storage container (10) is not moved so that the uppermost object in the pile is pressed against and adheres to the receiving surface (19), after which the pile is lowered again.

4 Claims, 3 Drawing Figures

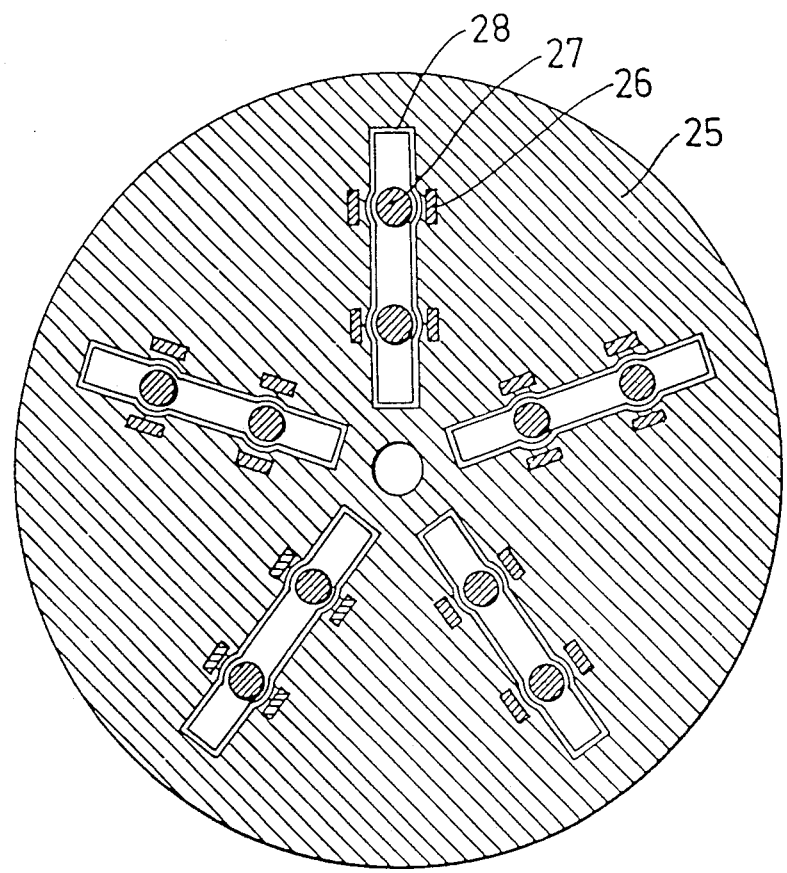

METHOD AND DEVICE FOR APPLICATION OF OBJECTS ONTO A SURFACE

This invention relates to a method and device for application of objects onto a receiving adhesive surface, especially for applying antibiotic patches or test strips onto an agar surface.

Several devices are known for applying antibiotic patches onto an agar surface. Most of these devices are provided with a plurality of magazines for patches, from which the antiobiotic patches are fed by means similar to a tongue. Substantially three methods for application of the patches are used.

According to a first method described e.g. in SE Pat. No. 381 103 and U.S. Pat. No. 3,934,753 the patches are allowed to fall freely onto the agar surface through a pipe which may be tapered. According to another method described in SE Pat. No. 403 520 and U.S. Pat. Nos. 3,836,047 and 4,042,145 a mechanism is used by means of which the antibiotic patches are thrust through the pipes down onto the agar surface.

Thus, at both these methods pipes are used through which the antibiotic patches will pass. The pipes end close to the agar surface. In order that they should not touch the surface, which might cause contamination of substances transferred by the end surface of the pipes from one part of the agar surface to another, these end surfaces are located at some distance above the edge of a Petri cup containing agar to eliminate the influence of different height of agar layer and edges. As too great a distance between pipe and agar surface may cause a less accurate application of the patches on the agar surface the distance must be kept as short as is compatible with avoiding the risk of contamination. However, this makes a short free fall of the patches necessary, by which these may be placed on their edges or hover away.

When these two known methods are used the antibiotic patches must, moreover, be pressed down manually after application to lie tightly against the agar surface.

As mentioned above, there is also a third method for application of antibiotic patches onto an agar surface which method has been developed so as to eliminate the disadvantages of the first and second methods and is described e.g. in SE Pat. No. 7811840-3 (418 165) and U.S. Pat. No. 4,286,730. According to this third method the antibiotic patch is given off to a receiving surface where a needle is put into the antibiotic patch which is transferred to the agar surface by the aid of the needle after which another means separated from the needle presses the antibiotic patch against the agar surface.

Certainly this method has succeeded in eliminating the disadvantages of the two first methods, but is complicated, and the device contains many movable parts and therefore its manufacture is expensive and also sensitive to disturbance.

It is the object of this invention to provide a method and a device by which the above-mentioned disadvantages can be avoided.

The above-mentioned object of the invention has been achieved in that the invention has been given the characteristic features defined in the claims.

Figure 2:
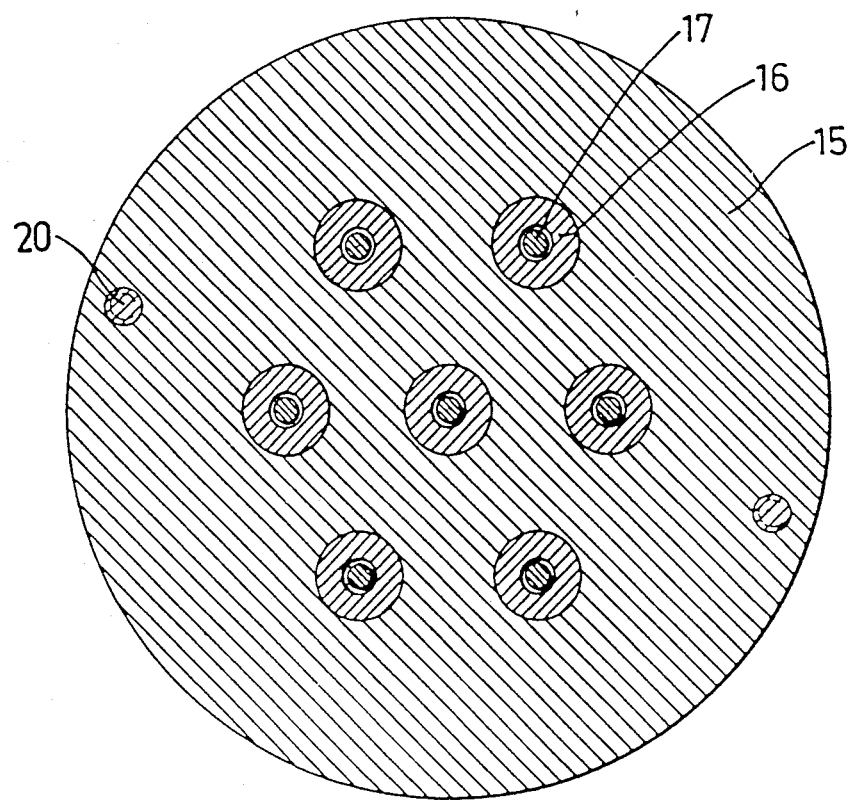

The invention is described more closely in the form of an illustrative example shown on the drawings, FIG. 1 showing a vertical section of a device according to the invention, FIG. 2 a horizontal section of the device taken along the arrows II—II in FIG. 1 and FIG. 3 showing a horizontal section of the device made to include storage containers and objects of another form than in FIG. 2.

The basic principle of the method and the device according to the invention is that the objects, e.g. test patches or test strips to be applied to a receiving adhesive surface are stored in a pile, the whole pile being lifted to press the uppermost objects in the pile against a downwardly directed receiving adhesive surface, e.g. an agar surface.

Thus, a device working according to this principle is shown in FIG. 1. A number of upwardly open pipes 10 of a non-magnetic material, e.g. glass, and containing each their pile of antibiotic patches 11 are arranged in recesses 12 in a fixed bottom plate 13. The pipes 10 pass freely through openings 14 in a vertically movable plate 15 arranged above the fixed bottom plate 13. In the movable plate 15 annular magnets 16 are arranged around the openings 14. Within the pipes 10 a ball 17 of magnetic material movable in the pipe, on which the antiobiotic patches rest, is arranged below the antiobiotic patches 11. When the movable plate 15 is moved away from the fixed plate 13 the balls 17 are also moved, due to the influence of the magnets 16, upwards in the pipes 10 and lift the piles of antibiotic patches 11 upwards towards a Petri cup 18 located above, turned upside down and having a downwardly directed agar surface 19.

For the displacement of the movable plate 15 a pair of vertically threaded rods 20 can be freely rotatably mounted in the fixed plate 13, said rods passing the displaceable plate 15 and co-operating with nuts 21 rigidly connected with the movable plate. The drive or rotation of the threaded rods 20 can e.g. be achieved by means of an electric motor not shown and driving chains or belts in engagement with gears or pulleys, non-rotatably connected with the threaded rods 20.

The drive of the threaded rods 20 is controlled by suitable means so that at each activation the threaded rods 20 are made to rotate so many turns that the displaceable plate 15 and consequently the piles of antiobiotic patches 11 are displaced so far upwards that the uppermost antibiotic patch in each pile is pressed against the agar surface 19. After this the threaded rods are attached in opposite direction to return to the starting position or a new starting position which, in that case, is as much higher than the previous starting position corresponding to the thickness of one antibiotic patch, the upward displacement each time being as great. At such a control it is suitable if the pitch of the threaded rods corresponds to the thickness of one antibiotic patch, the threaded rods at each activation being rotated n number of turns to displace the movable plate upwards and then rotated n-1 number of turns in opposite direction. One alternative of this control is that the threaded rods have a pitch corresponding to the thickness of one antibiotic patch and are rotated one turn at each activation whereby one cam surface causes the movable plate during this rotation to move the required distance towards the agar surface. This displacement of the movable plate need not be formed in the manners described here above but can also be embodied in other ways. However, the displacement should be such that the patches after each upward displacement towards the agar surface are again lowered to a protected position within the pipes, so that the patches in the piles e.g. cannot be blown away.

In FIG. 3 a horizontal section of a displaceable plate 25 is shown through which storage containers 28 of a substantially elongate rectangular cross section pass. In these storage containers 28 long and narrow strips (not shown) are piles and rest on two balls 27 of a magnetic material. Beside openings in the displaceable plate 25 of the storage containers 28 magnets 26 are disposed straight in front of the balls 27 to displace these in the storage containers 28 when the plate 25 is displaced relative to the storage containers. It is not necessary that the strips in this embodiment rest on balls but it is also possible to replace these with an elongate element of a magnetic material.

The patches or strips arranged in a pile allow of a certain compressibility, through which less differences in distance between the piles and the application surface can be bridged. The use of magnets outside the storage containers co-operating with elements located within the storage container gives a further reinforcement of this possibility as the magnets can be displaced longer even if the element within the storage container cannot do this which was not possible with a rigid displacement means within the storage container.

As is apparent from the claims the invention is not restricted to application of antibiotic patches onto an agar surface but can also be used for application of other types of objects on an adhesive surface. Of course the invention is not either restricted to application on a round surface but the application as well as the form of the fixed and displaceable plates can be other than round and the pattern for the placement of the storage containers in the plates and consequently the application onto the surface can be arbitrarily embodied and not restricted to what has been shown in the drawing figures.

What is claimed is:

1. A device for applying an object such as an antibiotic patch or a test strip onto a receiving downwardly turned adhesive surface, e.g. an agar surface, said device comprising: at least one upwardly open storage container for containing a pile of objects, said storage container including an element on which the pile of objects can rest, said element being vertically displaceable in said storage container; and means for displacing the object pile upwards in order to press the uppermost object in the pile against the surface, said means including at least one magnet vertically displaceable relative to the storage container arranged outside and adjacent said storage container.

2. A device as in claim 1 wherein a plurality of storage containers are arranged in a preselected pattern and are attached to a fixed plate, said device further comprising a displaceable plate oriented above the fixed plate and provided with recesses through which the storage containers pass and within which magnets are arranged.

3. A device as in claim 2 wherein the storage containers are tubular and the magnets are annular.

4. A device as in claim 2 including at least one threaded rod coacting with a nut attached to the displaceable plate is arranged for the displacement of the displaceable plate relative to the fixed plate.

* * * * *